United States Patent
Koseoglu

(10) Patent No.: US 11,591,278 B2
(45) Date of Patent: *Feb. 28, 2023

(54) INTEGRATED PROCESSES TO PRODUCE GASOLINE BLENDING COMPONENTS FROM LIGHT NAPHTHA

(71) Applicant: SAUDI ARABIAN OIL COMPANY, Dhahran (SA)

(72) Inventor: Omer Refa Koseoglu, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/330,592

(22) Filed: May 26, 2021

(65) Prior Publication Data
US 2021/0276933 A1 Sep. 9, 2021

Related U.S. Application Data

(63) Continuation of application No. 16/703,529, filed on Dec. 4, 2019, now Pat. No. 11,021,422.

(51) Int. Cl.
| | |
|---|---|
| C07C 7/13 | (2006.01) |
| C07C 2/76 | (2006.01) |
| C07C 4/04 | (2006.01) |
| C07C 5/393 | (2006.01) |
| C07C 5/22 | (2006.01) |
| C10G 57/00 | (2006.01) |
| C10G 61/06 | (2006.01) |
| C10L 1/16 | (2006.01) |

(52) U.S. Cl.
CPC .............. *C07C 7/13* (2013.01); *C07C 2/76* (2013.01); *C07C 4/04* (2013.01); *C07C 5/22* (2013.01); *C07C 5/393* (2013.01); *C10G 57/00* (2013.01); *C10G 61/06* (2013.01); *C10L 1/1691* (2013.01); *C07C 2521/06* (2013.01); *C07C 2529/70* (2013.01); *C10G 2300/1044* (2013.01); *C10G 2300/30* (2013.01); *C10L 2270/023* (2013.01)

(58) Field of Classification Search
CPC ....................................................... C07C 4/04
See application file for complete search history.

(56) References Cited

U.S. PATENT DOCUMENTS

| | | | | |
|---|---|---|---|---|
| 2011/0245556 | A1* | 10/2011 | Sohn ................. | C10G 9/36 |
| | | | | 585/650 |
| 2012/0074039 | A1* | 3/2012 | Gonzalez ........... | C10G 9/00 |
| | | | | 208/79 |
| 2018/0155638 | A1* | 6/2018 | Al-Ghamdi ........ | B01D 3/14 |

FOREIGN PATENT DOCUMENTS

CN 104974790 A * 10/2015

OTHER PUBLICATIONS

Machine translation CN 104974790. retrieved Jul. 14, 2020 (Year: 2020).*

* cited by examiner

*Primary Examiner* — Philip Y Louie
*Assistant Examiner* — Alyssa L Cepluch
(74) *Attorney, Agent, or Firm* — Osha Bergman Watanabe & Burton LLP

(57) ABSTRACT

A process for the treatment of a light naphtha feedstock that comprises normal paraffins and iso-paraffins may include separating the feedstock into a first iso-paraffin stream and a normal paraffin stream. The separating may be performed with 5A molecular sieves, a pressure of about 1-3 bars, and a temperature of 100-260° C. A product stream may be provided by subjecting the normal paraffin stream to at least one of steam cracking, isomerizing, and aromatizing.

15 Claims, 3 Drawing Sheets

INTEGRATED PROCESSES TO PRODUCE GASOLINE BLENDING COMPONENTS FROM LIGHT NAPHTHA

BACKGROUND OF INVENTION

Light naphtha, which is generally defined as a C5-C6 hydrocarbon feedstock, originates from routine refinery processes. Light naphtha is generally used as a feed for steam crackers for light olefin production, and as a blending stock for gasoline production. However, light naphtha is generally an undesirable gasoline blending component because of its low octane number and high vapor pressure. Thus, the transformation of light naphtha into value-added gasoline blending components is an ongoing challenge.

The transformation of light naphtha is rendered difficult by the inert nature of carbon-carbon and carbon-hydrogen bonds, which require elevated temperatures for processing, providing unfavorable thermodynamics, low selectivity and yields, and high cost. As refiners process lighter feeds, such as shale oil and condensates, the generation of light naphtha is increasing. Targets include the production of isoalkanes, olefins, and/or aromatics from light naphtha. These components generally provide a higher octane number and, thus, are more useful additives for gasoline compositions To date, options for processing light naphtha have been limited. Typical processes are depicted in FIGS. 1A-1B, which directly subject a light naphtha feedstock 10 to either steam cracking 110 (FIG. 1A) or isomerization 120 (FIG. 1B). The steam cracking 110 generates a cracked product stream 12 that mainly comprises $C_{2-4}$ olefins and methane, with smaller quantities of other products. The isomerization 120, in contrast, results in an isomerized product stream 14 that consists essentially of iso-paraffins (or "isomerate"), resulting in an increase in the research octane number (RON).

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to processes for treating a light naphtha feedstock that includes normal paraffins and iso-paraffins having 5 or 6 carbon atoms. The processes may include separating the feedstock into an iso-paraffin stream and a normal paraffin stream. The normal paraffin stream may be aromatized to produce an aromatic stream and a non-aromatic stream, and the non-aromatic stream may be subjected to steam cracking to provide an olefinic stream.

In a further aspect, embodiments disclosed herein relate to processes for treating a light naphtha feedstock that includes normal paraffins and iso-paraffins having 5 or 6 carbon atoms. The processes may include separating the feedstock into an iso-paraffin stream and a normal paraffin stream. The separation may be performed with 5 A molecular sieves, a pressure of about 1-3 bars, and a temperature of 100-260° C. A product stream may be provided by subjecting the normal paraffin stream to at least one of steam cracking, isomerizing, and aromatizing.

Other aspects and advantages of the claimed subject matter will be apparent from the following description and the appended claims.

DETAILED DESCRIPTION

Embodiments in accordance with the present disclosure generally relate to processes and systems for upgrading light naphtha to value added products. Generally, embodiments in accordance with the present disclosure involve an initial separation step that isolates iso-paraffins from normal paraffins. The normal paraffins may then be processed through one or more processes selected from the group consisting of steam cracking, isomerization, and aromatization.

Traditional processing of a naphtha feed stream may only use a naphtha splitter, which segregates different fractions according to boiling point ranges. However, as distinct hydrocarbon fractions may have boiling points that overlap, this method is insufficient for, for instance, separating iso-paraffins from normal paraffins. Therefore, naphtha processing is typically performed on a mixture of normal and iso-paraffins. However, the operation of a cracking unit works most efficiently with normal hydrocarbons, and so the presence of iso-paraffins decreases the efficiency of the cracking process. Further, if the naphtha feedstock is isomerized, the isomerization will also be less efficient as the light naphtha feedstock will already comprise a significant isomerate fraction.

For the purposes of the present disclosure, accompanying components that are conventionally used in light naphtha processing, such as air supplies, catalyst hoppers, gas handling apparatus, spent catalyst discharge sub-systems, catalyst replacement sub-systems, valves, temperature sensors, electronic controllers and the like, are not shown or discussed herein for sake of simplicity. One of ordinary skill in the art would appreciate that such components may be included in the embodiments disclosed herein.

Figure 2:
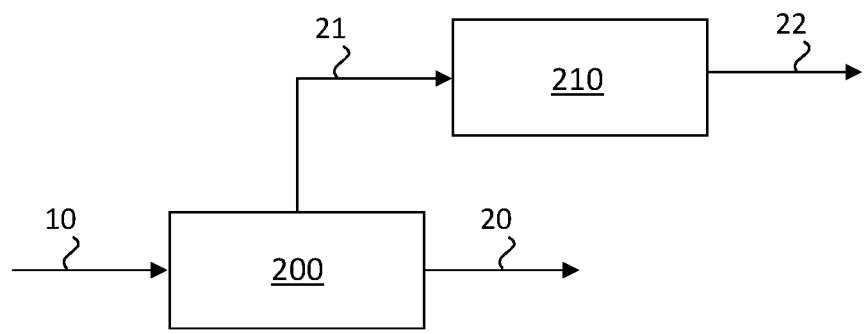
FIG. 2 is a schematic illustration depicting a process and system of one or more embodiments of the present disclosure.

FIG. 2 depicts a process and a system of one or more embodiments of the present disclosure, the system comprising a separation unit 200 and a cracking unit 210.

In one or more embodiments, a light naphtha feedstock 10 is fed into a separation unit 200. The light naphtha feedstock 10 of one or more embodiments may comprise a mixture of C5 and C6 hydrocarbons. In further embodiments, the light naphtha feedstock 10 may consist essentially of C5 and C6 hydrocarbons or consist of C5 and C6 hydrocarbons. In certain embodiments the feedstock 10 may have an initial boiling point of any of 10, 20, 30, 36, 40, 50, and 65° C., and a final boiling point of any of 75, 78, 80, 85, 90, 95, 100, and 110° C. In one or more embodiments, the feedstock 10 in accordance with the present disclosure may be a hydrocarbon fraction having a boiling point ranging from about 30 to 90° C. In further embodiments, the feedstock 10 in accordance with the present disclosure may be a hydrocarbon fraction having a boiling point ranging from about 36 to 78° C.

The light naphtha feedstock 10 of one or more embodiments may comprise at least a portion of iso-paraffins, saturated hydrocarbons with a branched-chain structure, and normal paraffins, saturated hydrocarbons with a straight-chain structure. In one or more embodiments, the feedstock 10 in accordance may comprise iso-paraffins in an amount ranging from about 30 to 70% by weight (wt. %). In some embodiments, the feedstock may comprise the iso-paraffins in an amount ranging from a lower limit of any of 30, 40, 45, and, 50 wt. % to an upper limit of any of 40, 45, 50, 55, 60, and 70 wt. %, where any lower limit can be used with any mathematically-compatible upper limit. In one or more embodiments, the feedstock 10 in accordance may comprise normal paraffins in an amount ranging from about 30 to 70% by weight (wt. %). In some embodiments, the feedstock may comprise the normal paraffins in an amount ranging from a lower limit of any of 30, 40, 45, and, 50 wt. % to an upper limit of any of 40, 45, 50, 55, 60, and 70 wt. %, where any lower limit can be used with any mathematically-compatible upper limit. In one or more embodiments, the feedstock 10 may be sourced from one or more of crude oil, a gas condensate, liquid coal, biofuels, and intermediary refinery processes.

The feedstock 10 of one or more embodiments may have a sulfur content of 10 parts per million by weight (ppmw) or less, 5 ppmw or less, 3 ppmw or less, 1 ppmw or less, 0.5 ppmw or less, less than 0.3 ppmw, or 0.1 ppmw or less. In one or more embodiments, the feedstock 10 may have a sulfur content of 100 ppmw or more, 1000 ppmw or more, 5000 ppmw or more, or 10000 ppmw or more.

The feedstock 10 of one or more embodiments may have a nitrogen content of 10 ppmw or less, 5 ppmw or less, 3 ppmw or less, 1 ppmw or less, 0.5 ppmw or less, less than 0.3 ppmw, or 0.1 ppmw or less.

In one or more embodiments the feedstock 10 is separated in a separation unit 200. The separation of one or more embodiments isolates the iso-paraffins of the feedstock from the normal paraffins. The separation provides an iso-paraffin stream 20 and a normal paraffin stream 21. In one or more embodiments, the iso-paraffin stream 20 may consist essentially of or, in some embodiments consist of, iso-paraffins. In one or more embodiments, the normal paraffin stream 21 may consist essentially of or, in some embodiments consist of, normal paraffins.

In one or more embodiments, a molecular sieve adsorption process is used to separate normal paraffins from iso-paraffins. In some embodiments, this separation method relies on the pore size of the molecular sieve to selectively adsorb normal paraffins due to the relatively smaller molecular diameter of normal paraffins compared to iso-paraffins. As would be appreciated by those having ordinary skill in the art, the adsorption step is followed by a desorption step for net recovery of normal paraffins. These steps may be performed cyclically or pseudocontinuously. In a pseudo-continuous process, a portion of the molecular sieves are cycled between the adsorption and desorption steps, while a remaining portion of the sieves are maintained under the separation conditions. One of ordinary skill in the art will appreciate, with the benefit of this disclosure, that the selection of a molecular sieve is dependent upon the identity, and relative sizes, of the normal and iso-paraffins. In one or more embodiments disclosed herein, the separation may comprise the use of a 5 A molecular sieve adsorbent.

In some embodiments, the separation step may separate straight chain C5 and/or C6 paraffins from branched C5 and/or C6 paraffins. In additional embodiments, not shown in FIG. 2, straight chain paraffins and singly branched C6 paraffins in the isomerate reaction mixture may be separated from C6 paraffins having two or more branches.

In one or more embodiments, the separation in accordance with the present disclosure may be performed at a pressure ranging from about 0.5 to 4 bar. In some embodiments, the separation may be performed at a pressure ranging from a lower limit of any of 0.5, 0.8, 1.0, 1.2, 1.5, and 1.8 bar to an upper limit of any of 2.2, 2.5, 2.8, 3.0, 3.5, and 4.0 bar, where any lower limit can be used with any mathematically-compatible upper limit. In particular embodiments, the separation in accordance with the present disclosure may be performed at a pressure ranging from about 1 to 3 bar.

In one or more embodiments, the separation 200 in accordance with the present disclosure may be performed at a temperature ranging from about 20 to 280° C. In some embodiments, the separation may be performed at a temperature ranging from a lower limit of any of 20, 50, 95, 100, 120, 140, 160, and 180° C. to an upper limit of any of 180, 200, 220, 240, 260, and 280° C., where any lower limit can be used with any mathematically-compatible upper limit. In particular embodiments, the separation in accordance with the present disclosure may be performed at a temperature ranging from about 100 to 260° C.

In one or more embodiments, after separation 200, the normal paraffin stream 21 may be fed to a steam cracking unit 210. Steam cracking is a petrochemical process in which saturated hydrocarbons, such as normal paraffins, are broken down into smaller, often unsaturated, hydrocarbons. The steam cracking process 210 detailed herein may produce various products, including lighter alkenes (olefins) such as ethylene, propylene, and butadiene, as well as methane and aromatics such as benzene and toluene.

In one or more embodiments, the normal paraffin stream 21 may be diluted with steam (not shown on FIG. 2) and then heated in an anaerobic furnace. After the cracking temperature has been reached, the gas is quickly quenched to stop the reaction in a transfer line exchanger. The products generated in the reaction, and their yield, generally depend on the composition of the feed, on the hydrocarbon to steam ratio and on the cracking temperature (which may be very high), and furnace residence time (which may be very short). Generally, higher cracking temperatures favor the production of ethylene and benzene, whereas lower temperatures produce relatively higher amounts of propene, C4-hydrocarbons, and liquid products.

In one or more embodiments, the steam cracking in accordance with the present disclosure may be performed at a temperature ranging from about 600 to 1000° C. In some embodiments, the steam cracking may be performed at a temperature ranging from a lower limit of any of 600, 700, 750, 775, 800, 825, and 850° C. to an upper limit of any of 850, 875, 900, 950, and 1000° C., where any lower limit can be used with any mathematically-compatible upper limit. In particular embodiments, the steam cracking in accordance with the present disclosure may be performed at a temperature ranging from about 700 to 900° C. In particular embodiments, the steam cracking in accordance with the present disclosure may be performed at a temperature of approximately 800° C.

In one or more embodiments, the steam cracking in accordance with the present disclosure may be performed at a pressure ranging from about 0.8 to 1.5 bar. In some embodiments, the steam cracking may be performed at a pressure ranging from a lower limit of any of 0.8, 0.9, 1.0, 1.1, and 1.2 bar to an upper limit of any of 1.0, 1.1, 1.2, 1.3, 1.4, and 1.5 bar, where any lower limit can be used with any mathematically-compatible upper limit. In particular embodiments, the steam cracking in accordance with the present disclosure may be performed at a pressure ranging of approximately 1 bar.

In one or more embodiments, the steam cracking in accordance with the present disclosure may be performed at a steam to hydrocarbon ratio ranging from about 0.1:1 to 0.8:1 by weight. In some embodiments, the steam cracking may be performed at a steam to hydrocarbon ratio ranging from a lower limit of any of 0.1:1, 0.2:1, 0.3:1, 0.4:1, 0.5:1, and 0.6:1, by weight, to an upper limit of any of 0.5:1, 0.6:1, 0.7:1, and 0.8:1, by weight, where any lower limit can be used with any mathematically-compatible upper limit. In particular embodiments, the steam cracking in accordance with the present disclosure may be performed at a steam to hydrocarbon ratio of approximately 0.6:1 by weight.

In one or more embodiments, the steam cracking in accordance with the present disclosure may be performed with a residence time of less than 1 second. In some embodiments, the steam cracking may be performed with a residence time ranging from a lower limit of any of 0.01, 0.10, 0.20, 0.30, 0.35, and 0.40 seconds to an upper limit of any of 0.40, 0.50, 0.60, 0.75, and 1.0 seconds, where any lower limit can be used with any mathematically-compatible upper limit. In particular embodiments, the steam cracking in accordance with the present disclosure may be performed with a residence time of approximately 0.35 seconds.

The steam cracking 210 of one or more embodiments may produce a steam-cracked product stream 22. The product stream 22 may comprise a portion of light ($C_{2-4}$) olefins. In some embodiments, the product stream may comprise light olefins in an amount of 30 wt. % or more, 40 wt. % or more, or 50 wt. % or more. In some embodiments, the product stream may comprise light olefins in an amount ranging from about 40 to 60 wt. % or, in particular embodiments, about 45 to 55 wt. %. In one or more embodiments, the product stream 22 may comprise an aromatic portion that may include one or more of benzene, toluene, and xylenes. In some embodiments, the product stream may comprise an aromatic portion in an amount of 20 wt. % or less. In some embodiments, the product stream 22 may comprise the aromatic portion in an amount ranging from about 5 to 15 wt. %. The cracked product stream may be treated, recovered and further processed by any method, and for any use, known to one of ordinary skill in the art.

The iso-paraffin stream 20 may be treated, recovered and further processed by any method, and for any use, known to one of ordinary skill in the art. In some embodiments, finished gasoline may be produced by blending at least a portion of the iso-paraffin stream with other gasoline components, such as one or more of butanes, butenes, pentanes, naphtha, catalytic reformate, isomerate, alkylate, polymer, aromatic extract, heavy aromatics, gasoline from catalytic cracking, hydrocracking, thermal cracking, thermal reforming, steam pyrolysis and coking, oxygenates such as methanol, ethanol, propanol, isopropanol, tert-butyl alcohol, sec-butyl alcohol, methyl tertiary butyl ether, ethyl tertiary butyl ether, methyl tertiary amyl ether and higher alcohols and ethers, and small amounts of additives to provide a desired property.

Figure 3:
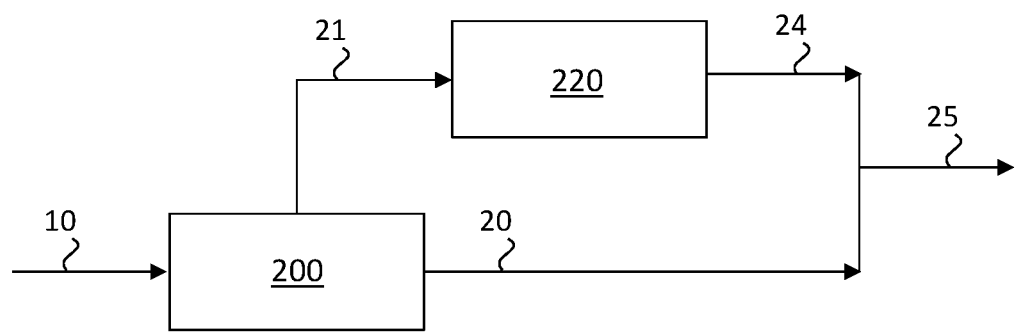
FIG. 3 is a schematic illustration depicting a process and system of one or more embodiments of the present disclosure.

FIG. 3 depicts a process and a system of one or more embodiments of the present disclosure, the system comprising a separation unit 200 and an isomerization unit 220. It is noted that component 200 and feeds 10, 20, and 21 are the same as discussed above with regard to FIG. 2 and, though their description is not repeated, each stream, component, and condition described above is also present in the embodiment shown in FIG. 3

Generally, the processes represented by FIG. 3 differ from those represented by FIG. 2, discussed above, in that the normal paraffin stream 21 is fed to an isomerization unit 220 where it is isomerized, rather than the steam cracking unit 210 of FIG. 2.

In one or more embodiments, an isomerization in accordance with the present disclosure will increase the RON of the hydrocarbon mixture, and comprises mixing the normal paraffin stream 21 with an excess of hydrogen gas (not shown in FIG. 3) to dissolve a portion of the hydrogen gas in the liquid hydrocarbon feedstock to produce a hydrogen-enriched liquid hydrocarbon feedstock and reacting the normal paraffins to produce isomerates. The normal paraffin stream 21 of one or more embodiments may have a RON of 60 or less, of 50 or less, or of 45 or less.

The isomerization unit may have any suitable configuration known to one of ordinary skill in the art. In some embodiments, the unit can include one or more fixed-bed, moving-bed, fluidized-bed, or batch reactor systems. The isomerization reaction zone may include a single reactor or multiple reactor configurations with suitable fluid communication between reactors and thermal means and control to ensure that the desired isomerization temperature is maintained at the inlet to each zone.

In one or more embodiments, the isomerization may use any suitable catalyst known to a person of ordinary skill in the art. The isomerization catalysts of one or more embodiments may include, but are not limited to, those that are amorphous, for example comprising amorphous alumina, or zeolitic, such as platinum on alumina, a zeolite, a chlorinated alumina, a sulfated zirconia and platinum, a platinum group metal on chlorided alumina, a tungstated support of a Group IVB oxide or hydroxide. In one or more embodiments the catalyst may comprise 0.05 wt. % to 5 wt. % of a Group VIIIB metal. In some embodiments, the catalyst may comprise a base material, such as zeolite or alumina, and one or more Group IIIB or IVB metal oxides. In particular embodiments, the catalyst may be a zirconia-based catalyst. As used herein, the term "zeolite" includes not only aluminosilicates but variants in which the aluminum is replaced by other trivalent elements and/or silicon is replaced by other tetravalent elements.

In one or more embodiments, the isomerization in accordance with the present disclosure may be performed at a pressure ranging from about 10 to 100 bar. In some embodiments, the isomerization may be performed at a pressure ranging from a lower limit of any of 10, 20, 30, 35, 40, and 50 bar to an upper limit of any of 45, 50, 60, 70, 80, 90, and 100 bar, where any lower limit can be used with any mathematically-compatible upper limit. In particular embodiments, the isomerization in accordance with the present disclosure may be performed at a pressure of approximately 40 bar.

In one or more embodiments, the isomerization in accordance with the present disclosure may be performed at a hydrogen to hydrocarbon mole ratio ($H_2$:HC) ranging from about 0.01:1 to 20:1. In some embodiments, the isomerization may be performed at a $H_2$:HC ranging from a lower limit of any of 0.01:1, 0.02:1, 0.03:1, 0.04:1, 0.05:1, and 0.10:1, to an upper limit of any of 0.06:1, 0.08:1, 0.10:1, 0.20:1, 0.50:1, 1:1, 5:1, 10:1, and 20:1, where any lower limit can be used with any mathematically-compatible upper limit. In particular embodiments, the steam cracking in accordance with the present disclosure may be performed at a $H_2$:HC of approximately 0.05:1.

In one or more embodiments, the isomerization may be performed with a liquid hourly space velocity (LHSV) ranging from a lower limit of any of 0.2, 0.5, 1.0, and 1.5 $h^{-1}$ to an upper limit of any of 1.5, 2.0, 5.0, and 20 $h^{-1}$, where any lower limit can be used with any mathematically-compatible upper limit. In particular embodiments, the isomerization in accordance with the present disclosure may be performed with a LHSV of approximately 1.5 $h^{-1}$.

In one or more embodiments, the isomerization in accordance with the present disclosure may be performed at a temperature ranging from about 20 to 300° C. In some embodiments, the isomerization may be performed at a temperature ranging from a lower limit of any of 20, 50, 80, 100, 120, 140, 160, and 180° C. to an upper limit of any of 180, 200, 220, 240, 260, and 300° C., where any lower limit can be used with any mathematically-compatible upper limit. In particular embodiments, the isomerization in accordance with the present disclosure may be performed at a temperature of approximately 160° C. In some embodiments, lower reaction temperatures may be preferred to favor equilibrium mixtures having the highest concentration of high-octane highly branched iso-paraffins and to minimize cracking of the feed to lighter hydrocarbons. One of ordinary skill in the art would appreciate, with the benefit of this disclosure, that the temperature and other conditions are also partially determined by the type of catalyst used.

In some embodiments, the isomerization conditions in the isomerization may be maintained at levels effective to maintain at least about 90% by volume of the normal paraffin stream 21 in liquid phase. In particular embodiments, the isomerization is performed under conditions effective to increase the RON of the normal paraffin stream 21. In some embodiments, the resulting iso-paraffin stream 24 may have a RON of 75 or more, of 80 or more, of 85 or more, or of 90 or more. The iso-paraffin stream 24 of one or more embodiments may comprise a significant isomerate portion. In some embodiments, the resulting iso-paraffin stream 24 may comprise isomerates in an amount of 80 wt. % or more, 90 wt. % or more, 95 wt. % or more, or 99 wt. % or more. In some embodiments, the iso-paraffin stream may consist essentially of, or in other embodiments consist of, isomerates.

The iso-paraffin stream 24 may be treated, recovered and further processed by any method, and for any use, known to one of ordinary skill in the art. The stream 24 may be treated the same as, or different from, stream 20. In one or more embodiments, the stream 24 may be combined 25 with the iso-paraffin stream 20. In some embodiments, finished gasoline may be produced by blending at least a portion of the iso-paraffin stream 24 with other gasoline components, such as one or more of butanes, butenes, pentanes, naphtha, catalytic reformate, isomerate, alkylate, polymer, aromatic extract, heavy aromatics, gasoline from catalytic cracking, hydrocracking, thermal cracking, thermal reforming, steam pyrolysis and coking, oxygenates such as methanol, ethanol, propanol, isopropanol, tert-butyl alcohol, sec-butyl alcohol, methyl tertiary butyl ether, ethyl tertiary butyl ether, methyl tertiary amyl ether and higher alcohols and ethers, and small amounts of additives to provide a desired property.

Figure 4:
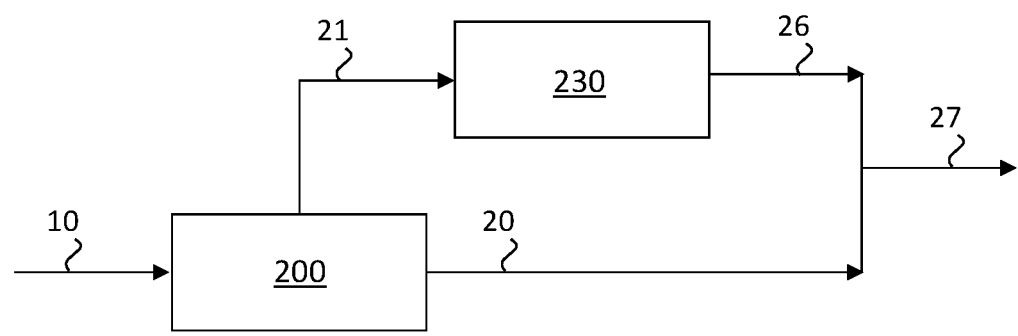
FIG. 4 is a schematic illustration depicting a process and system of one or more embodiments of the present disclosure.

FIG. 4 depicts a process and a system of one or more embodiments of the present disclosure, the system comprising a separation unit 200 and an aromatization unit 230. It is noted that component 200 and feeds 10, 20, and 21 are the same as discussed above with regard to FIGS. 2 and 3 and, though their description is not repeated, each stream, component, and condition described above is also present in the embodiment shown in FIG. 4.

Generally, the processes represented by FIG. 4 differ from those represented by FIGS. 2 and 3, discussed above, in that the normal paraffin stream 21 is fed to an aromatization unit 230 where it is aromatized, rather than the steam cracking unit 210 of FIG. 2 or the isomerization unit 220 of FIG. 3.

In one or more embodiments, the aromatization of the present disclosure may be any such process known to one of ordinary skill in the art that is suitable for converting normal paraffins into a product stream rich in one or more of benzene, toluene and xylenes, and light hydrocarbon gases. Benzene and xylenes are useful petrochemical building blocks for many chemical and polymer materials. In one or more embodiments, the aromatization 230 generates an aromatic-rich stream 26.

In one or more embodiments, the aromatization in accordance with the present disclosure may be performed at a pressure ranging from about 0.5 to 80 bar. In some embodiments, the aromatization may be performed at a pressure ranging from a lower limit of any of 0.5, 0.8, 1.0, 1.5, 5, 10, and 20 bar to an upper limit of any of 1.2, 1.5, 2, 5, 10, 25, 50, and 80 bar, where any lower limit can be used with any mathematically-compatible upper limit. In particular embodiments, the aromatization in accordance with the present disclosure may be performed at a pressure of approximately 1 bar.

In one or more embodiments, the aromatization may be performed with a liquid hourly space velocity (LHSV) ranging from a lower limit of any of 0.2, 0.5, 1.0, and 1.5 $h^{-1}$ to an upper limit of any of 1.5, 2.0, 5.0, and 20 $h^{-1}$, where any lower limit can be used with any mathematically-compatible upper limit. In particular embodiments, the aromatization in accordance with the present disclosure may be performed with a LHSV of approximately 1 $h^{-1}$.

In one or more embodiments, the aromatization may be performed with any suitable aromatization catalyst known to one of ordinary skill in the art. In some embodiments, the catalyst may be a zeolite. In particular embodiments a MFI type zeolite catalyst may be used. The catalyst of one or more embodiments may be used in either a moving bed or a fixed bed.

In one or more embodiments, the aromatization in accordance with the present disclosure may be performed at a temperature ranging from about 200 to 700° C. bar. In some embodiments, the aromatization may be performed at a temperature ranging from a lower limit of any of 200, 300, 400, 500, and 550 C to an upper limit of any of 500, 550, 600, and 700° C., where any lower limit can be used with any mathematically-compatible upper limit. In particular embodiments, the aromatization in accordance with the present disclosure may be performed at a temperature of approximately 550° C.

The aromatization of one or more embodiments may generate an aromatic-rich stream 26, which comprises a portion of one or more of benzene, toluene, xylenes. In some embodiments, the aromatic-rich stream 26 may comprise benzene in an amount ranging from about 5 to 10 wt. %. In some embodiments, the aromatic-rich stream 26 may comprise xylenes in an amount ranging from about 5 to 10 wt. %. In some embodiments, the aromatic-rich stream 26 may comprise no substantial quantity of toluene. In one or more embodiments, the aromatic-rich stream 26 comprises an aromatics content of 10 wt. % or more, 15 wt. % or more, 20 wt. % or more, or 25 wt. % or more. In some embodiments, the aromatic-rich stream 26 comprises an aromatics content of 80 wt. % less, 60 wt. % or less, 40 wt. % or more, or 20 wt. % or less. In one or more embodiments, the aromatic-rich stream 26 is passed downstream for additional processing and separations, including petrochemical processing. The aromatics-rich steam 26 of one or more embodiments may comprise an unreacted portion of the normal paraffins of stream 21. The unreacted paraffins may constitute the aromatics-rich steam 26 in an amount of 30 wt. % or less, 20 wt. % or less, or 10 wt. % or less. The aromatics-rich steam 26 of one or more embodiments may further comprise a portion of light ($C_{2-4}$) olefins and, in some embodiments, be combined 27 with the iso-paraffin stream 20.

Figure 5:
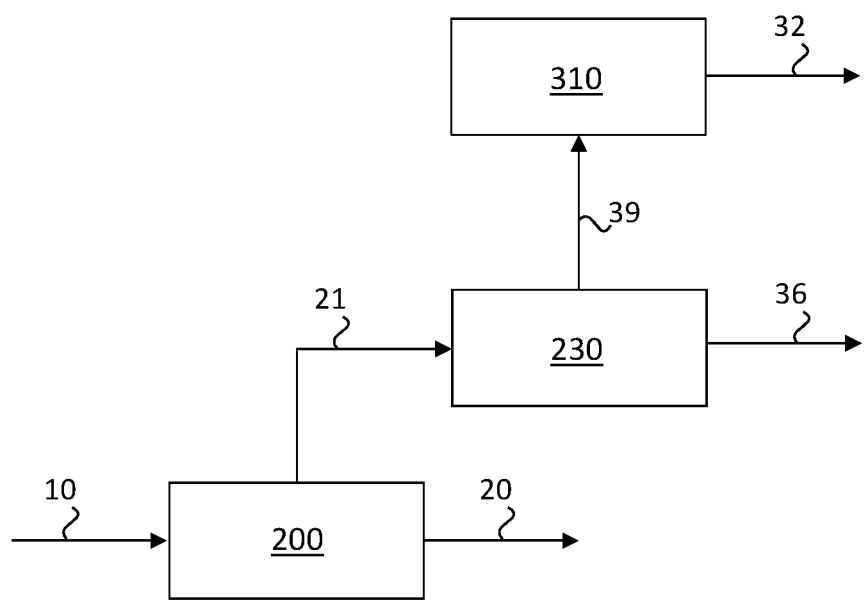
FIG. 5 is a schematic illustration depicting a process and system of one or more embodiments of the present disclosure.

FIG. 5 depicts a process and a system of one or more embodiments of the present disclosure, the system comprising a separation unit 200, an aromatization unit 230, and a cracking unit 310. It is noted that components 200 and 230, and feeds 10, 20, and 21 are the same as discussed above with regard to FIGS. 2-4 and, though their description is not repeated, each stream, component, and condition described above is also present in the embodiment shown in FIG. 3.

Generally, the processes represented by FIG. 5 differ from those represented by FIG. 4, discussed above, in that the aromatization unit 230 provides two streams: an aromatic stream 36 and a non-aromatic stream 39, which is subsequently subjected to steam cracking 310, rather than the aromatization of FIG. 4 that provides only one aromatic-rich stream.

In one or more embodiments, the aromatization 230 of the normal paraffin stream 21 produces a variety of hydrocarbon components. Such components comprise one or more aromatics, including one or more of the group consisting of benzene, toluene and xylene. The aromatization of some embodiments further provides one or more of an unreacted portion of the normal paraffins of stream 21, an isomerate portion, and a portion of light ($C_{2-4}$) olefins. In some embodiments, the aromatics may be separated and removed from the aromatization unit 230 as an aromatic stream 36. The aromatics may be separated from the other components by any method known to the art, including fractionation. The remaining products of aromatization are sent as a non-aromatic stream 39 to a steam cracking unit 310.

The aromatic stream 36 of one or more embodiments may consist essentially of one or more of benzene, toluene, and xylenes. In some embodiments, the aromatic stream 36 may consist of a mixture of one or more of benzene, toluene, and xylenes. In some embodiments, the aromatic stream 36 comprises benzene in an amount ranging from 40 to 60 wt. %. In some embodiments, the aromatic stream 36 comprises xylenes in an amount ranging from 40 to 60 wt. %.

The non-aromatic stream 39 may comprise an unreacted portion of the normal paraffins of stream 21. The non-aromatic stream may comprise unreacted paraffins in an amount of 30 wt. % or less, 20 wt. % or less, or 10 wt. % or less. The non-aromatic stream 39 may comprise an isomerate portion, which in some embodiments may constitute the non-aromatic stream 39 in an amount of 30 wt. % or less, 20 wt. % or less, or 10 wt. % or less. The non-aromatic stream 39 of one or more embodiments may further comprise a portion of light ($C_{2-4}$) olefins.

In one or more embodiments, the non-aromatic stream 39 may be steam cracked. The steam-cracking 310 may be performed in accordance with any of the conditions and configurations discussed previously regarding the steam cracking 210 of FIG. 2. The steam cracking generates an olefinic stream 32. The olefinic stream 39 may comprise a significant portion of ethylene in addition to other light olefins and aromatics. The olefinic stream 39 may be treated by any method known by one of ordinary skill in the art, and passed downstream for additional processing and separations, including petrochemical processing.

Examples

The following examples are merely illustrative and should not be interpreted as limiting the scope of the present disclosure.

To illustrate the effect of separation on the product composition provided by some of the aforementioned embodiments, Comparative Examples 1 and 2 and Examples 1-4 are given below. Reported in Tables 1-6 are the material balances (by mass) for each Example, as obtained by simulations (Examples 1 and 4 and Comp. Ex 1-2) and experiments (Examples 2-3).

Example 1 was prepared by a process in accordance with one or more embodiments represented by FIG. 2, involving a paraffin separation step and subsequent steam cracking of a normal paraffin stream. The separation was performed at a pressure of 1-3 bars, with a proprietary molsieve 5 A adsorbent, and at a temperature of 100-260° C. The steam cracking was performed at a temperature of 800° C., a pressure of 1 bar, a steam-to-hydrocarbon weight ratio of 0.6:1, and a residence time of 0.35 seconds.

TABLE 1

Material Balance for Example 1 (streams labelled as per FIG. 2)

| Stream# | 10 | 21 | 20 | 22 |
|---|---|---|---|---|
| Light Naphtha | 80,000 | | | |
| Isomerate | | | 38,640 | |
| Paraffins | | 41,360 | | |
| Hydrogen | | | | 620 |
| Methane | | | | 7,114 |
| Ethane | | | | |
| Ethylene | | | | 13,897 |
| Propane | | | | |
| Propylene | | | | 6,452 |
| Butadiene | | | | 1,861 |
| Other C4 | | | | 1,737 |
| Benzene | | | | 2,771 |
| Toluene | | | | 1,406 |
| Xylenes | | | | |
| Pyrolysis Gasoline | | | | 3,557 |
| Fuel oil | | | | 1,944 |
| Total | 80,000 | 41,360 | 38,640 | 41,360 |
| RON | 62.3 | 43.1 | 82.8 | NA |

Example 2 was prepared by a process in accordance with one or more embodiments represented by FIG. 3, involving a paraffin separation step and subsequent isomerization of a normal paraffin stream. The separation was performed as for Example 1. The isomerization was performed at a temperature of 160° C., an outlet pressure of 40 bar, a $H_2$:hydrocarbon mole ratio of 0.05:1, a LHSV of 1.5 $h^{-1}$, and with a zirconia commercial catalyst.

TABLE 2

Material Balance for Example 2 (streams labelled as per FIG. 3)

| Stream# | 10 | 21 | 20 | 24 | 25 |
|---|---|---|---|---|---|
| Light Naphtha | 80,000 | | | | |
| Isomerate | | | 38,640 | 40,946 | 79,586 |
| Paraffins | | 41,360 | | | — |
| Hydrogen | | | | | — |
| Methane | | | | | — |
| Ethane | | | | | |
| Ethylene | | | | | — |
| Propane | | | | | |
| Propylene | | | | | — |
| Butadiene | | | | | |
| Other C4 | | | | | |
| Benzene | | | | | |
| Toluene | | | | | — |
| Xylenes | | | | | |
| Pyrolysis Gasoline | | | | | — |
| Fuel oil | | | | | — |
| Total | 80,000 | 41,360 | 38,640 | — | 79,586 |
| RON | 62.3 | 43.1 | 82.8 | NA | 82.8 |

Example 3 was prepared by a process in accordance with one or more embodiments represented by FIG. 4, involving a paraffin separation step and subsequent aromatization of a normal paraffin stream. The separation was performed as for Example 1. The aromatization was performed at a temperature of 550° C., an outlet pressure of 1 bar, a LHSV of 1 h$^{-1}$, and with a MFI-type zeolite catalyst.

TABLE 3

Material Balance for Example 3 (streams labelled as per FIG. 4)

| Stream# | 10 | 21 | 20 | 26 | 27 |
|---|---|---|---|---|---|
| Light Naphtha | 80,000 | | | | |
| Isomerate | | | 38,640 | 7,607 | 46,247 |
| Paraffins | | 41,360 | | 8,577 | 8,577 |
| Hydrogen | | | | — | — |
| Methane | | | | 1,386 | 1,386 |
| Ethane | | | | 3,344 | 3,344 |
| Ethylene | | | | 2,179 | 2,179 |
| Propane | | | | 5,923 | 5,923 |
| Propylene | | | | 2,447 | 2,447 |
| Butadiene | | | | — | — |
| Other C4 | | | | 3,771 | 3,771 |
| Benzene | | | | 3,082 | 3,082 |
| Toluene | | | | — | — |
| Xylenes | | | | 3,044 | 3,044 |
| Pyrolysis Gasoline | | | | — | — |
| Fuel oil | | | | — | — |
| Total | 80,000 | 41,360 | 38,640 | 41,360 | 80,000 |
| RON | 62.3 | 43.1 | 82.8 | NA | 82.8 |

Example 4 was prepared by a process in accordance with one or more embodiments represented by FIG. 5, involving a paraffin separation step and subsequent aromatization of a normal paraffin stream. The aromatization gives a non-aromatic stream that is then steam cracked. The separation, aromatization, and steam cracking were performed as for Examples 1-3.

TABLE 4

Material Balance for Example 4 (streams labelled as per FIG. 5)

| Stream# | 10 | 21 | 20 | 39 | 36 | 32 |
|---|---|---|---|---|---|---|
| Light Naphtha | 80,000 | | | | | |
| Isomerate | | | 38,640 | 7,607 | | |
| Paraffins | | 41,360 | | 8,577 | | |
| Hydrogen | | | | | | 768.0 |
| Methane | | | | 1,386 | | 7311.6 |
| Ethane | | | | 3,344 | | 0.0 |
| Ethylene | | | | 2,179 | | 12896.3 |
| Propane | | | | 5,923 | | 0.0 |
| Propylene | | | | 2,447 | | 4637.9 |
| Butadiene | | | | | | 1176.8 |
| Other C4 | | | | 3,771 | | 1182.9 |
| Benzene | | | | | 3,082 | 1440.2 |
| Toluene | | | | | | 630.6 |
| Xylenes | | | | | 3,044 | 291.3 |
| Pyrolysis Gasoline | | | | | | 1508.9 |
| Fuel oil | | | | | | 760.6 |
| Total | 80,000 | 41,360 | 38,640 | 35,233 | 6,127 | 32,605 |
| RON | 62.3 | 43.1 | 82.8 | 82.8 | NA | NA |

Figure 1A:
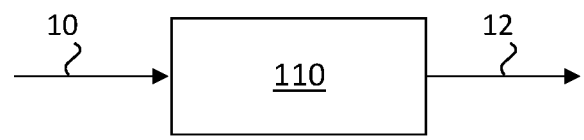
FIGS. 1A-B are schematic illustrations that depict prior art processes for processing light naphtha.

Comparative Example 1 was prepared by a process in accordance with one or more embodiments represented by FIG. 1A, involving steam cracking a light naphtha feed. The steam cracking was performed as for Example 1.

TABLE 5

Material Balance for Comp. Example 1 (streams labelled as per FIG. 1A)

| Stream# | 10 | 12 |
|---|---|---|
| Light Naphtha | 80,000 | |
| Isomerate | | |
| Paraffins | | |
| Hydrogen | | 1,200 |
| Methane | | 13,760 |
| Ethane | | — |
| Ethane | | 26,880 |
| Propane | | — |
| Propylene | | 12,480 |
| Butadiene | | 3,600 |
| Other C4 | | 3,360 |
| Benzene | | 5,360 |
| Toluene | | 2,720 |
| Xylenes | | |
| Pyrolysis Gasoline | | 6,880 |
| Fuel oil | | 3,760 |
| Total | 80,000 | 80,000 |
| RON | 62.28 | NA |

Figure 1B:
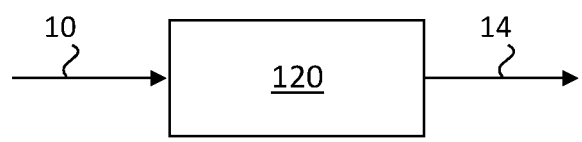

Comparative Example 2 was prepared by a process in accordance with one or more embodiments represented by FIG. 1B, involving isomerizing a light naphtha feed. The isomerization was performed as for Example 2.

TABLE 6

Material Balance for Comp. Example 2 (streams labelled as per FIG. 1B)

| Stream# | 10 | 14 |
|---|---|---|
| Light Naphtha | 80,000 | |
| Isomerate | | 79,897 |
| Paraffins | | |
| Hydrogen | | |
| Methane | | |
| Ethane | | |
| Ethylene | | |
| Propane | | |

TABLE 6-continued

Material Balance for Comp. Example 2
(streams labelled as per FIG. 1B)

| Stream# | 10 | 14 |
|---|---|---|
| Propylene | | |
| Butadiene | | |
| Other C4 | | |
| Benzene | | |
| Toluene | | |
| Xylenes | | |
| Pyrolysis Gasoline | | |
| Fuel oil | | |
| Total | 80,000 | 79,897 |
| RON | 62.3 | 82.0 |

Although the preceding description has been described herein with reference to particular means, materials and embodiments, it is not intended to be limited to the particulars disclosed herein; rather, it extends to all functionally equivalent structures, methods and uses, such as are within the scope of the appended claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed is:

1. A process for treatment of a light naphtha feedstock, the process comprising:
   separating the light naphtha feedstock comprising normal paraffins and iso-paraffins having 5 or 6 carbon atoms into an iso-paraffin stream and a normal paraffin stream consisting of paraffins having 5 and 6 carbon atoms, wherein the iso-paraffin stream is sent to a gasoline pool; and
   at least one of steam cracking and aromatizing the normal paraffin stream to produce a product stream.

2. The process of claim 1, wherein the feedstock consists essentially of the normal paraffins and iso-paraffins having 5 or 6 carbon atoms.

3. The process of claim 1, wherein the separating is performed with 5 A molecular sieves.

4. The process of claim 1, wherein the separating is performed at a pressure ranging from about 1-3 bar.

5. The process of claim 1, wherein the separating is performed at a temperature ranging from 100-260° C.

6. The process of claim 1, wherein the aromatizing is performed with a MFI zeolite catalyst.

7. The process of claim 1, wherein the aromatizing is performed at a temperature of 500-600° C.

8. The process of claim 1, wherein the steam cracking is performed at a temperature of 750-850° C.

9. The process of claim 1, wherein the steam cracking is performed with a steam-to-hydrocarbon ratio ranging from 0.5:1 to 0.7:1 by weight.

10. A process for treatment of a light naphtha feedstock, the process comprising:
    separating the feedstock comprising normal paraffins and iso-paraffins into a first iso-paraffin stream and a normal paraffin stream consisting of 5 and 6 carbon atoms with 5 A molecular sieves at a pressure of about 1-3 bars and a temperature of 20-260° C.; and
    aromatizing the normal paraffin stream to produce an aromatic stream and a non-aromatic stream.

11. The process of claim 10, wherein the separating is performed at a temperature in a range from 20° C. to about 180° C.

12. The process of claim 10, wherein the feedstock consists essentially of the normal paraffins and iso-paraffins having 5 or 6 carbon atoms.

13. The process of claim 10, wherein the first iso-paraffin stream is sent to a gasoline pool.

14. The process of claim 10, further comprising steam cracking the non-aromatic stream to provide an olefinic stream.

15. The process of claim 14, wherein the steam cracking is performed with a steam-to-hydrocarbon ratio ranging from 0.5:1 to 0.7:1 by weight and at a temperature of 750-850° C.

* * * * *